(12) United States Patent
Krüger et al.

(10) Patent No.: US 11,559,642 B2
(45) Date of Patent: Jan. 24, 2023

(54) OPERATING UNIT FOR A VENTILATOR WITH A GAS DISPENSING DEVICE FOR VENTILATION GASES

(71) Applicant: Drägerwerk AG & Co. KGaA, Lübeck (DE)

(72) Inventors: Thomas Krüger, Lübeck (DE); Dinesh Singh, Lübeck (DE); Michael Gömann, Lübeck (DE); Simone Wortelen, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 284 days.

(21) Appl. No.: 17/097,816

(22) Filed: Nov. 13, 2020

(65) Prior Publication Data

US 2021/0146072 A1 May 20, 2021

(30) Foreign Application Priority Data

Nov. 20, 2019 (DE) .......................... 102019008044.0

(51) Int. Cl.
*G08B 23/00* (2006.01)
*A61M 16/00* (2006.01)
(Continued)

(52) U.S. Cl.
CPC ...... *A61M 16/0051* (2013.01); *A61M 16/026* (2017.08); *G06F 3/016* (2013.01);
(Continued)

(58) Field of Classification Search
CPC ............ A61M 16/0051; A61M 16/026; A61M 2016/0027; A61M 2205/502;
(Continued)

(56) References Cited

U.S. PATENT DOCUMENTS 5,669,379 A * 9/1997 Somerson ............. A61M 16/00
128/204.21
8,757,152 B2 * 6/2014 Milne ..................... G06F 3/011
128/204.23
(Continued)

FOREIGN PATENT DOCUMENTS

DE 19500529 A1 8/1996
DE 102017122045 A1 3/2019
(Continued)

OTHER PUBLICATIONS

Hamilton Medical, Bedienhandbuch Hamilton-C6, Aug. 15, 2017; pp. 1-388.

*Primary Examiner* — Tai T Nguyen
(74) *Attorney, Agent, or Firm* — McGlew and Tuttle, P.C.

(57) ABSTRACT

An operating unit (2) sets ventilation parameters of a control unit (11) of a ventilator (1) that includes a gas dispensing device (10) for ventilation gases. The operating unit includes a display unit and an ventilation parameters input element (23, 24). Two or more of the parameters are linked via a relation condition stored in a relation storage module (40). A relation monitor (3) includes a deviation detector (31) detecting a transgression of the relation condition during parameter setting, and outputs warning information via a warning unit (32). This avoids a need for an operator to note the sometimes complicated connections and dependencies expressed in the relations during the parameter setting. The warning may be sent before the new setting value is sent from the operating unit to the control unit. Operating safety is increased and a risk of setting errors is minimized.

15 Claims, 7 Drawing Sheets

(51) Int. Cl.
  *G06F 3/01* (2006.01)
  *G06F 3/04847* (2022.01)
  *G09G 5/377* (2006.01)
  *G08B 21/04* (2006.01)

(52) U.S. Cl.
  CPC ..... *G06F 3/04847* (2013.01); *G08B 21/0423* (2013.01); *G09G 5/377* (2013.01); *A61M 2016/0027* (2013.01); *A61M 2205/502* (2013.01); *A61M 2230/435* (2013.01); *G09G 2380/08* (2013.01)

(58) Field of Classification Search
  CPC .............. A61M 2230/435; G06F 3/016; G06F 3/04847; G08B 21/0423; G09G 5/377; G09G 2380/08
  USPC ...................................................... 340/573.1
  See application file for complete search history.

(56) References Cited

U.S. PATENT DOCUMENTS 8,924,878 B2 * 12/2014 Palmer .................. G06F 3/0488
  715/764
2009/0241958 A1 10/2009 Baker, Jr.
2015/0160845 A1 6/2015 Lahtivuori et al.

FOREIGN PATENT DOCUMENTS

WO 2015027980 A2 3/2015
WO 2019057641 A1 3/2019

* cited by examiner

Lower PEEP/ Higher FiO$_2$

| FiO$_2$ | 0,3 | 0,4 | 0,4 | 0,5 | 0,5 | 0,6 | 0,7 | 0,7 |
|---|---|---|---|---|---|---|---|---|
| PEEP | 5 | 5 | 8 | 8 | 10 | 10 | 10 | 12 |

| FiO$_2$ | 0,7 | 0,8 | 0,9 | 0,9 | 0,9 | 1,0 |
|---|---|---|---|---|---|---|
| PEEP | 14 | 14 | 14 | 16 | 18 | 18 - 24 |

Higher PEEP/ Lower FiO$_2$

| FiO$_2$ | 0,3 | 0,3 | 0,3 | 0,3 | 0,3 | 0,4 | 0,4 | 0,5 |
|---|---|---|---|---|---|---|---|---|
| PEEP | 5 | 8 | 10 | 12 | 14 | 14 | 16 | 16 |

| FiO$_2$ | 0,5 | 0,5 - 0,8 | 0,8 | 0,9 | 1,0 | 1,0 |
|---|---|---|---|---|---|---|
| PEEP | 18 | 20 | 22 | 22 | 22 | 24 |

OPERATING UNIT FOR A VENTILATOR WITH A GAS DISPENSING DEVICE FOR VENTILATION GASES

CROSS REFERENCE TO RELATED APPLICATIONS

This application claims the benefit of priority under 35 U.S.C. § 119 of German Application 10 2019 008 044.0, filed Nov. 20, 2019, the entire contents of which are incorporated herein by reference.

TECHNICAL FIELD

The present invention pertains to an operating unit for setting at least two parameters for a ventilator that are relevant to the ventilation with a gas dispensing device for ventilation gases. The operating unit comprises a display unit for outputting the parameters as well as an input element for changing a preselected parameter, which is selected from the parameters that are relevant to the ventilation

TECHNICAL BACKGROUND

Ventilators and anesthesia devices for supplying patients with breathing gas as well as possibly with other medical gases are known. Patients are connected to these devices, and ventilation parameters and ventilation modes are set at the devices. The devices have, for this purpose, a control unit with an operating unit, by means of which the ventilation parameters and ventilation modes can be set and monitored. In practice, these are often touch-sensitive flat display screens (touchscreens) which are possibly combined with a physical input element, for example, a rotary knob, a button, a rotary actuator/pressure actuator or the like.

Provisions may be made, for example, for the operation such that the user first selects a ventilation parameter to be changed at the operating unit by means of a menu structure, e.g., selects by means of a rotary actuator, selects the ventilation parameter to be changed by pressing on a confirmation switch, changes the selected ventilation parameter in terms of value as desired and then finally confirms the ventilation parameter reset in this way by pressing on an input element, as a result of which it is accepted as a new setting value for the ventilator. Such an operating unit is known, e.g., from DE 195 00 529 A1 and has proved successful in practice.

However, often not only one parameter, but a plurality of parameters have to be adjusted. For faster adjustment, it has been proposed to optionally dispense with an acknowledgment and use the value set at the rotary actuator immediately, see DE 10 2004 03879 B3. Skipping over acknowledgment saves times, which is advantageous especially in case of a rapid consecutive input of a plurality of parameters.

However, especially in case of setting a plurality of parameters, it should be noted that these can be set individually separately from one another, but there are frequently certain dependencies between the parameters. The result is that the individual parameters may not be changed in relation to one another as desired. For example, certain restrictions between the ventilation parameters FiO2 and PEEP should thus be noted for a sufficient oxygenation of ventilated patients. For example, certain lower limits and upper limits for the setting of the PEEP should thus be noted in case of a certain FiO2. Such relations between ventilation parameters are determined by expert committees and have been published, e.g., by the US-American ARDSnet Committee (see FIGS. 13 and 14). For the sake of patient safety, these values, i.e., especially the relations described therewith should be met during the setting of the ventilation parameters.

Since the setting of individual ventilation parameters may already be critical for the patient, there is a risk that the operator of the ventilator does not have a full view in all directions and possibly does not observe the sometimes complicated connections between the different ventilation relations in case of manual setting. This may lead to considerable risks to the health of the patient.

SUMMARY

An object of the present invention is to create an improved operating unit for a ventilator, with which this risk is reduced.

In an operating unit for a ventilator that comprises a gas dispensing device for ventilation gases and a gas dispensing-influencing and-monitoring control unit, wherein the operating unit is configured to set at least two parameters of the control unit which are relevant to the ventilation and to send setting values for the parameters to the control unit, wherein the operating unit comprises a display unit for outputting the parameters as well as an input element for changing a preselected parameter, which is selected from the parameters that are relevant to the ventilation, wherein, after the change, a new setting value is sent to the control unit for these selected parameters, a relation monitor is provided according to the present invention, which comprises     a relation storage module, in which at least one relation condition is stored between two or more of the parameters,     a deviation detector, which is configured to check the at least one relation condition to one or more of the other parameters when changing the preselected parameter and to detect whether the at least one relation condition is met or transgressed, and     a warning unit that interacts with the deviation detector and outputs corresponding warning information to an operator in case of a transgression, wherein a graphics module, which is configured to display the at least one relation condition, and especially the transgressed relation condition, as a preferably temporary fading in on the display unit by means of a superimposed view, is further provided for the relation monitor.

The core of the present invention is an automated analysis and user-friendly presentation of relevant ventilation parameter relations, briefly referred to as relations below, even during the actual setting of the selected parameter. The user-friendly presentation may be carried out, for example, such that setting data of one or more ventilation parameters are displayed on the display device, e.g., as a system of coordinates, the axes of which each stand for one of the parameters of a relation. Further, permissible and/or optimal combinations can be visualized as a graph in the system of coordinates. A special feature of the present invention is now that it is checked in an automated manner by the relation monitor whether or not the change made during the setting is permissible according to the relations even during the setting, i.e., before a new setting value is sent to the control unit. It can thus still be determined in due time in an automated manner whether or not the value currently set by the operator is consistent with the ventilation parameter relations before the acceptance of a new setting value for the selected parameter. In the latter case, a transgression of the relation condition is detected, and the operator is warned correspondingly, e.g., optically by a special marking in the superimposed view and/or by an acoustic signal, so that he can correct the setting value before he confirms the new setting value for sending to the control unit.

Since it is thus checked in an automated manner whether the currently set new setting value abides by the relations concerning the other ventilation parameters, and a warning is carried out in case of the transgression before sending to the control unit, an unintentional exceeding of the permissible individual range and transgression of the ventilation parameter relations can no longer occur. This gives the operator additional security and thus increases the quality of the setting of the ventilation parameters, which is ultimately a benefit to ventilation quality overall and thus to patient safety.

Moreover, the present invention thus makes it possible to act securely and rapidly in dynamically demanding situations, as they may occur, e.g., during surgery. A rapid and secure resetting even of a plurality of parameters is often decisive here for a good surgical outcome. The present invention offers valuable protection against possibly critical setting errors and thus acts in a manner which reduces the risk to the patient especially in such dynamic situations, which involve an increased risk of operating errors.

Thus, the present invention protects against a setting error, in which ventilation parameter relations are transgressed. The result is thus an improvement in setting quality and patient safety. This does not adversely affect the setting speed. On the contrary, the present invention makes it easy for the operator to reset even a plurality of parameters rapidly one after the other as needed, since he does not have to make new and possibly relatively complicated considerations each time regarding the meeting of the relations concerning the other ventilation parameters.

The graphics module is preferably configured such that the superimposed view is movable on the display unit. In this connection, the superimposed view is preferably placed such that it is always adjacent to a display view of the preselected parameter. This makes possible a dynamic positioning of the superimposed view. Due to its proximity in space to the preselected parameter, it visualizes at the same time at which parameter the current setting is made and transgression of the ventilation parameter relation may develop and/or can be resolved by a suitable setting.

Furthermore, the graphics module is preferably further configured to highlight a current value of the preselected parameter with a marking in case of the transgression of the relation condition. In this manner, the user can easily detect when the current setting of the selected parameter would lead to a transgression of the relation condition. This happens in an intuitively easily identifiable manner by highlighting the marking, especially by means of a color change, contrast color, symbol change, additional symbol and/or change of a background color; it is also possible to switch back and forth between different types of marking and/or warning sounds with different high frequencies may be outputted in order to thus further increase the alertness of the operator. The alertness of the operator is thus securely drawn toward the possibly imminent transgression of the relation. The risk of an unintentional setting error can thus be minimized.

According to the present invention, a view is provided, in which the current value of the preselected parameter is shown highlighted with a marking in a system of coordinates. In this case, the system of coordinates can be shown with coordinate axes or be suggested without coordinate axes through its view. The marking herein advantageously represents both the current value of the preselected parameter and the relation condition, especially the transgressed relation condition. Due to the view of the current value, it is illustrated to the operator what the magnitude of the set value is, on the one hand, and how its position is related to the system of coordinates shown, on the other hand. This facilitates both an intuitive recognition and an immediate detection, in which direction the value to be changed is, in order to meet the relation condition again.

In regard to the display of the relation condition, the graphics module is advantageously configured such that it can be displayed selectively visually, especially as a value corridor and/or as a target corridor in a system of coordinates. This enables the operator to make a simple and intuitive visual recognition, which promotes the detection rate and the decision for an appropriate response. It shall not be ruled out, however, that the relation condition is shown, as an alternative or in addition, as a value table.

In the relation storage module, at least one relation condition is contained between two ventilation parameters. To this end, the relation storage module advantageously has storage elements for one or more characteristics, lookup tables and/or especially multidimensional characteristic diagrams. According to the present invention, a relation condition is stored in the reaction storage module between the inspiratory oxygen fraction (FiO2) and the positive end-expiratory pressure (PEEP).

Provisions are preferably made for the relation storage module and/or the deviation detector to be configured for multiparameter relations as well. These are defined as relations which exist between more than two ventilation parameters and/or a plurality of relations between two or more ventilation parameters. Complicated relations between the different ventilation parameters can thus be imaged as well and can be monitored comfortably by the relation monitor for the operator.

A command element which interacts with the deviation detector is advantageously further provided. The command element is configured to form and to display a signal for the corrected setting of the preselected parameter, with which the transgression of the relation condition is eliminated. Thus, the operator receives in an automated manner from the command element information not only about whether a transgression of the relation condition is present, but also a recommendation for which parameter is to be changed in order to avoid the transgression of the relation condition. The operator is thus offered a valuable support in order to avoid critical situations at the outset and/or to be able to leave them again rapidly. This is a considerable advantage for the safety of the patient, especially in the surgical or intensive care setting.

A verification unit which interacts with the deviation detector and outputs a confirmation signal if a deviation is no longer present may advantageously be provided. The user thus immediately receives information if the transgression of the relation condition no longer exists. He is thus freed from the task of having to monitor the display permanently, but can concentrate on the surgery and change in the parameters until the confirmation signal finally provides him with information that the possibly critical transgression of the relation condition has now ended. The alertness of the operator can thus be focused entirely on the necessary change in the parameters. This represents a considerable advantage during the surgery as well as a significant increase in safety.

The confirmation signal preferably comprises an audio signal, animation, symbol change and/or a color change, especially a marking and/or a background.

The operating element advantageously comprises a virtual setting element on the display unit, and additionally at least one target mark, which represents an optimal value and/or limit for meeting the relation condition, is outputted on the display unit. This is especially, but not only, suitable for such an operating unit, which has no physical actuating element, e.g., those with a touchscreen operation. In this case, the operator can rapidly and purposefully set the desired value by tapping the desired setting value or by scrolling a scale of the virtual setting element. Further, it is made possible in this case to display a target value on the virtual setting element, for example, for a setting value which is considered to be optimal; the operator then only needs to select it and set it by tapping. This makes the operation easier and, moreover, prevents an operating error.

Provisions may, however, also be made, as an alternative or in addition, to configure the operating element as a physical actuating element, especially as a rotary knob, a pivot lever and/or a rotary actuator and/or pressure actuator. Such a physical actuator offers the operator a familiar feeling of setting and further offers a high protection against unintentional operating errors, since a physical movement is necessary for actuation.

An additional advantage with regard to intuitive operability is obtained by a counter-actuator being preferably associated with the operating element, which counter-actuator is configured to counteract further actuation of the operating element, for example, in the manner of a force feedback actuator. The counter-actuator preferably acts mechanically on the operating element, especially via a force action and/or torque action, which is directed against the actuation by the operator. Thus, the user receives a feedback about the setting made by him via the operating element. The risk of especially unintentional input errors or setting errors is thus reduced. This preferably occurs unidirectionally only in the direction of a further transgression of the relation condition. This acts on the operator in an especially intuitive manner and thus motivates the operator to return from a transgressed relation condition. A transgression of the relation condition may thus already be prevented in the making and/or a deepening of the transgression may thus be prevented. Due to the unidirectional mode of action, the user receives a clear feedback about the direction in which the parameter shall no longer be adjusted, but that it shall be adjusted into the opposite direction in order to thus reach values, at which the transgression of the relation condition no longer exists. Thanks to this unidirectionality, the counter-actuator offers a guiding function, which leads the operator out of the transgression of the relation condition again. It is especially advantageous when the counter-actuator generates a haptic feedback signal to the operator.

A haptic feedback signal is, however, not mandatory. Provisions may also be made for the counter-actuator to act functionally on the operating element by it reducing a control signal generated by the operating element, especially by changing a control characteristic of the operating element, and/or by actively countercontrolling said control characteristic, especially by means of an at least partial correction signal. This is especially suitable in actuators that are not physical, but are configured as a virtual setting element. Thus, the advantages of a physical "force feedback" may also be used in virtual setting elements.

Optionally, a default transmitter with a storage device may further be provided, which is configured to set the preselected parameter to a security value and to send a signal concerning this preferably separately in case of a transgression of the relation condition. It is thus possible to achieve that the transgression of the relation condition is eliminated by means of the security value set by the default transmitter in the absence of a response from the operator. "Default" is defined here as no setting value being predefined by the operator, so that alternatively a different value is to be used, namely the security value. The security value may be, for example, the last previous value, with which also preferably no transgression of the relation condition was present, or a limit value for the preselected parameter, which just still meets the transgressed relation condition. In order to inform the operator that the transgression of the relation condition was resolved by the default transmitter automatically, so to say, a separate signaling is advantageously carried out. The operator is thus informed that the operating unit has now made the setting for him.

It is especially advantageous when a storage device for previous setting values of the parameters is provided, wherein a history marker is provided, which selects at least one previous value for the selected parameter from the storage device and displays it on the display device. The most recently used setting values can thus be displayed. It is especially preferred if the history marker is further configured to display not only the individual values, but also the course of the most recently used setting values. The number of the most recent setting value to be displayed is preferably selectable in this case. Different colors or different symbolic highlights may be selected for the display of the course; as an alternative or in addition, the older values may also be displayed visually contiguously as a graph corresponding to the chronological sequence, e.g., connected by arrows, and/or they are provided with time data. It can thus be detected at a glance what course the previously set values have taken. This is especially favorable for detecting trends, for example, in order to detect early when getting close to critical limits and thus the transgression of one or more relations is imminent.

A predictor module is advantageously provided, which is configured to determine a suggested value for a value, which is to be set as the next value, of the preselected parameter from current and/or previous setting values of the parameters which are relevant to the ventilation. This is preferably implemented by means of prediction algorithms which are known per se. The operator is thus given an effective support in the selection of the setting value, which further reduces the risk of operating errors. As an alternative or in addition, current and/or previous patient measured values may also be used. For this purpose, the predictor module advantageously interacts with a measuring unit for patient measured values. The patient measured values especially include patient-related parameters such as the carbon dioxide exhaled by the patient ($CO_2$ partial pressure), pulse rate, blood pressure, oxide saturation actually reached especially in the arterial blood and the like. Thus, all in all, the setting of the parameters which are relevant to the ventilation can be coordinated, on the one hand, more flexibly and, on the other hand, also better with the current status of the patient.

Furthermore, a target mark generator, which interacts with the predictor module and is configured to display a symbol for a corresponding suggested value determined by the predictor module on the display device in the superimposed view, is preferably provided. In this way, the operator receives a direct and easily identifiable display of the new setting value, preferably by means of a display as an arrow and/or especially a flashing time. A both rapid and reliable setting of the new setting value can thus be achieved. Especially not only one, but also a plurality of target marks can be determined and a target mark on each of the characteristics can be displayed, for example, in the case of a relation defined by a plurality of characteristics, especially by a family of characteristics. The operator thus receives a selection. If the relation comprises, for example, a lower characteristic and an upper characteristic, then the corresponding target mark is displayed on both characteristics—the operator may then set one of the two.

Further, in case of a transgressed relation condition, a compensation module that determines a new setting value for the other parameters of the relation condition, with which the relation condition is then still met, may advantageously be provided. In this case, the fact that two or more parameters are involved in the relation condition is used. A transgressed relation condition can thereby often be resolved in two different ways, namely, on the one hand, by modification of the selected parameter per se, the adjustment of which has led to transgression of the relation condition or else, on the other hand, often also by an adjustment of the other parameter of the relation condition in order to meet the relation condition again. This may be advantageous if the adjustment that led to a transgression of the relation condition was necessary for an important, especially medically important, reason and the transgression cannot hence be eliminated by resetting this parameter; the compensation module in such a case may then suggest for the other parameters of the relation a new setting value, with which the transgression may likewise be eliminated. The compensation module is configured to determine this value. This is advantageously embodied by a reverse function of the relation condition being implemented in the compensation module. Another advantageous application for the compensation module is when a rapid adjustment is necessary, so that the one parameter can be adjusted manually rapidly, and the compensation module then follows the other parameter automatically in order to avoid a transgression of the relation condition. Thus, instead of two adjustments, only one adjustment is needed, which makes possible an overall faster adjustment while simultaneously meeting the relation condition. This may especially also be advantageous for an adjustment in the area of a jump in a desired characteristic: An adjustment that is too large per se in the case of a parameter, e.g., the parameter on the y axis of the characteristic diagram, is no longer transgressed if the other parameter, i.e., the parameter of the x axis in the example, is also sufficiently increased. A faster adjustment can thus be achieved especially in the area of an abrupt characteristic curve, which is otherwise difficult to handle.

In this connection, the compensation module advantageously interacts with an adjustment indicator generator, which displays a symbol for a corresponding adjustment of the other parameter on the display device. Thus, a signal regarding the value that the other parameter of the relation condition has to assume can be sent to the operator. The other parameter can then be set to this value manually or by means of the compensation module. The adjustment indicator generator spares the user from determining the value for the other parameter, with which a transgression of the relation condition can still be avoided. This also is also favorable for the rapidity and security of the adjustment.

Further, provisions may be advantageously provided for the operating unit to be arranged separated in space from the ventilator, and/or for a second operating unit separated in space to be provided, which is configured as a double of the operating unit. This makes possible the operation also from a desktop located elsewhere, e.g., from a remote desktop over the network of a hospital.

The present invention is explained below on the basis of an advantageous exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
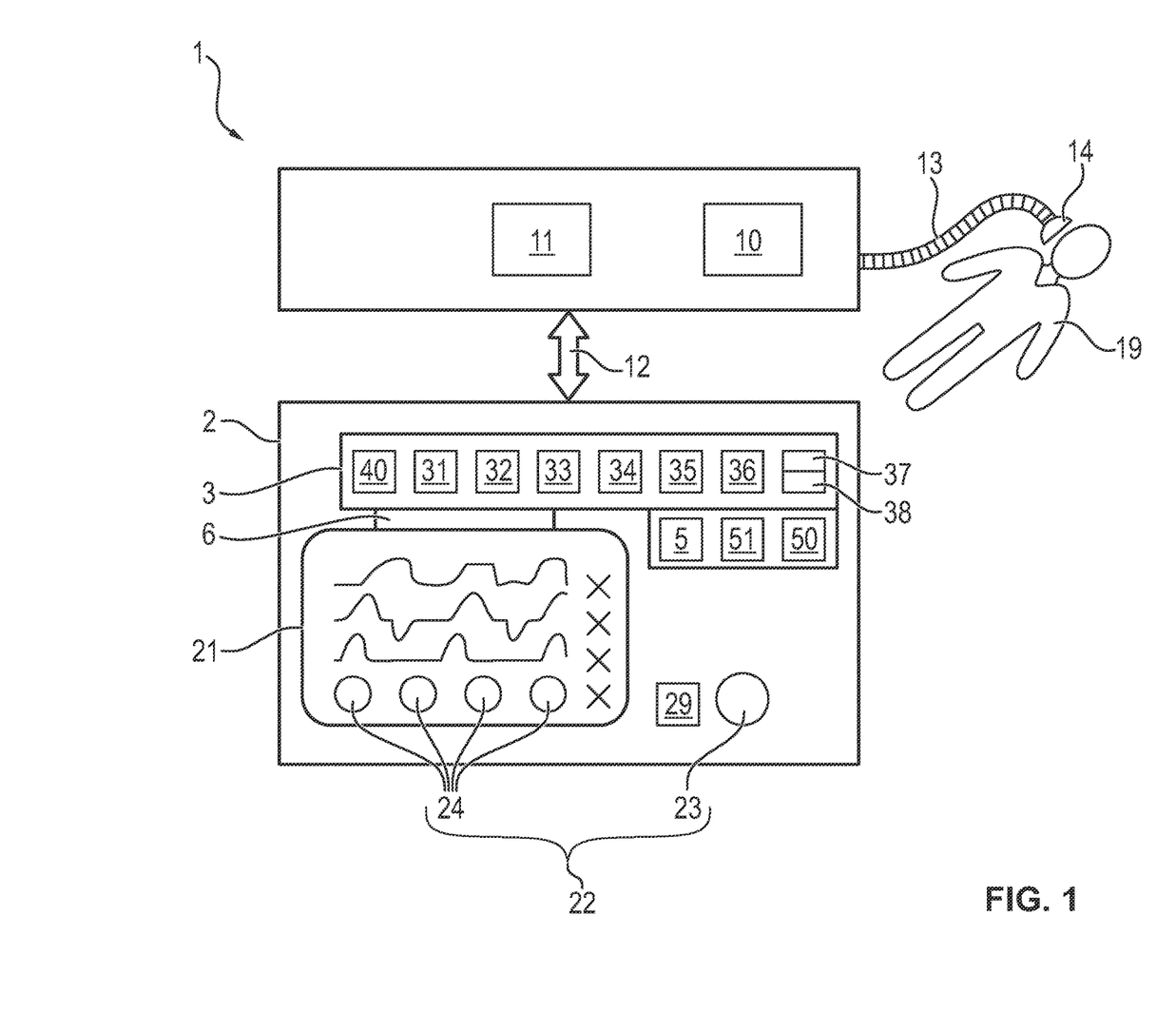
FIG. 1 is a schematic view of a ventilator with an operating unit.

Referring to the drawings, FIG. 1 schematically shows a ventilator 1 with an operating unit 2 according to an exemplary embodiment of the present invention. As principal components, the ventilator 1 comprises a control device 11 as well as a gas dispensing device 10, which is connected to a breathing mask 14 of a patient 19 via a combined inspiration and expiration line 13. The control device 11 is connected to the operating unit 2 via a connecting line 12. The control device 11 as well as the gas dispensing device 10 are configured in a manner known per se, so that they will not be explained in more detail below.

Figure 2:
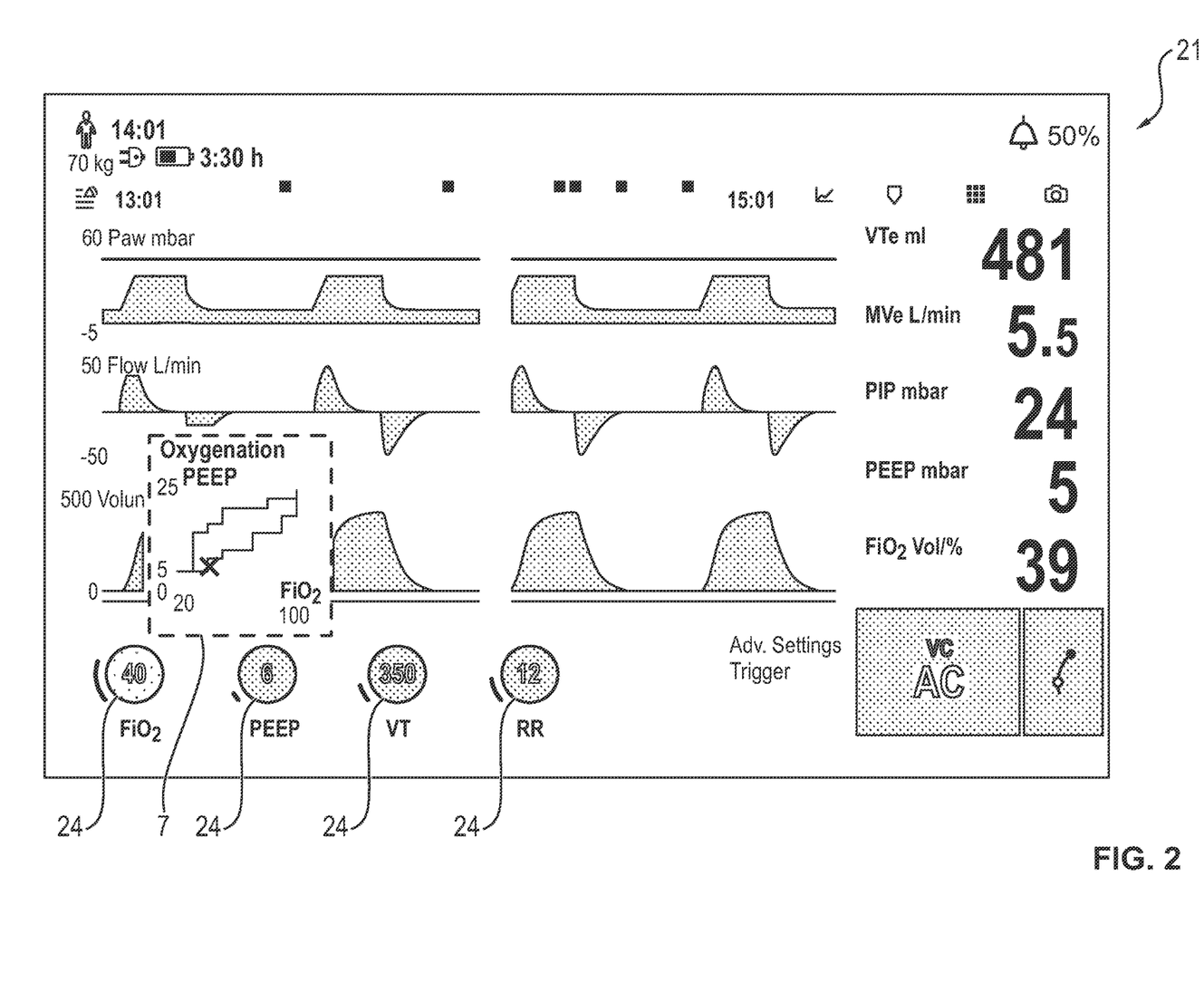
FIG. 2 is a view of a display on a display unit of the operating unit.

The operating unit 2 comprises a display unit 21 for outputting parameters, which is configured as a touchscreen in the embodiment being shown. Further, at least one input element 22 is provided, which may be configured as a physical, mechanical actuator 23 as well as as its virtual actuator 24 on the touchscreen (see FIG. 4). Necessary entries are made with the actuators 23, 24 and are sent to the control device 11. Correspondingly, the display unit 21 displays parameters of the operating unit 2 as well as parameters that are sent by the control device 11. An example of such a display is contained in FIG. 2, without a pop-up window 7 defined by the dotted line. It is seen that time curves for pressure, volume flow and tidal volume are displayed graphically in the main area of the display, various parameters that are relevant to the ventilation are displayed numerically in the right-hand area and four virtual actuators 24 are arranged in the lower area for setting ventilation parameters. The parameters set in such a manner are displayed on the display unit 21 and after confirmation are possibly sent to the control unit 11 of the ventilator 1, which in turn continuously returns updated parameters for display on the display unit 21. Since such operating units 2 and their interaction with the control device 11 are known from the state of the art, this does not need to be explained in more detail below.

According to the present invention, the operating unit 2 further comprises a relation monitor 3, which has a relation storage module 40, a deviation detector 31 as well as a warning unit 32. As is shown in more detail in FIG. 3, the relation storage module 40 has a plurality of storage elements 41, 42, 43, in each of which at least one relation 4 between ventilation parameters is stored.

Figure 3:
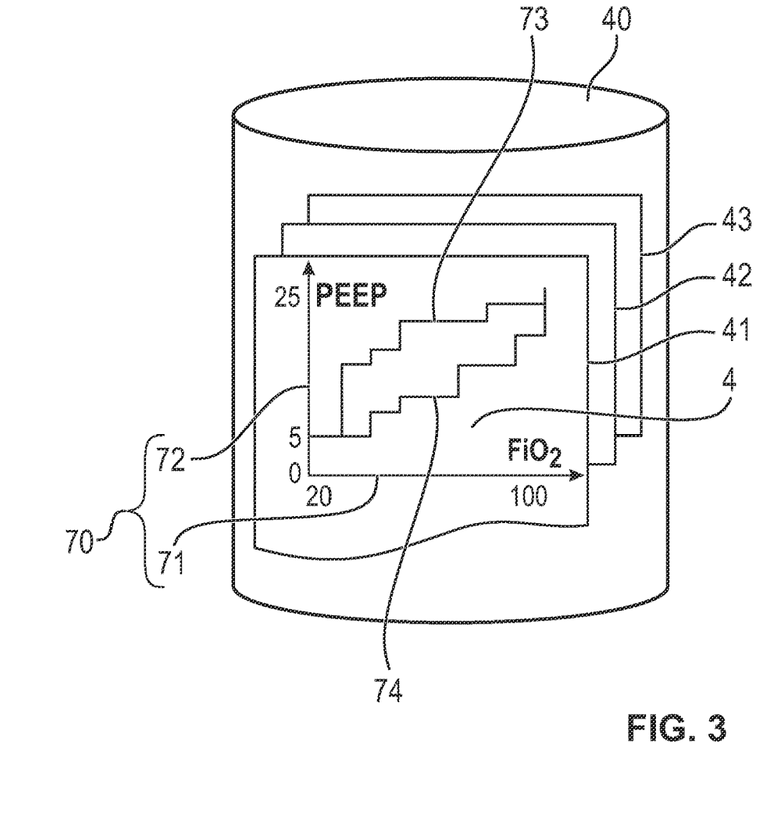
FIG. 3 is a schematic view of a relation storage module with stored relation.
Figure 11A:
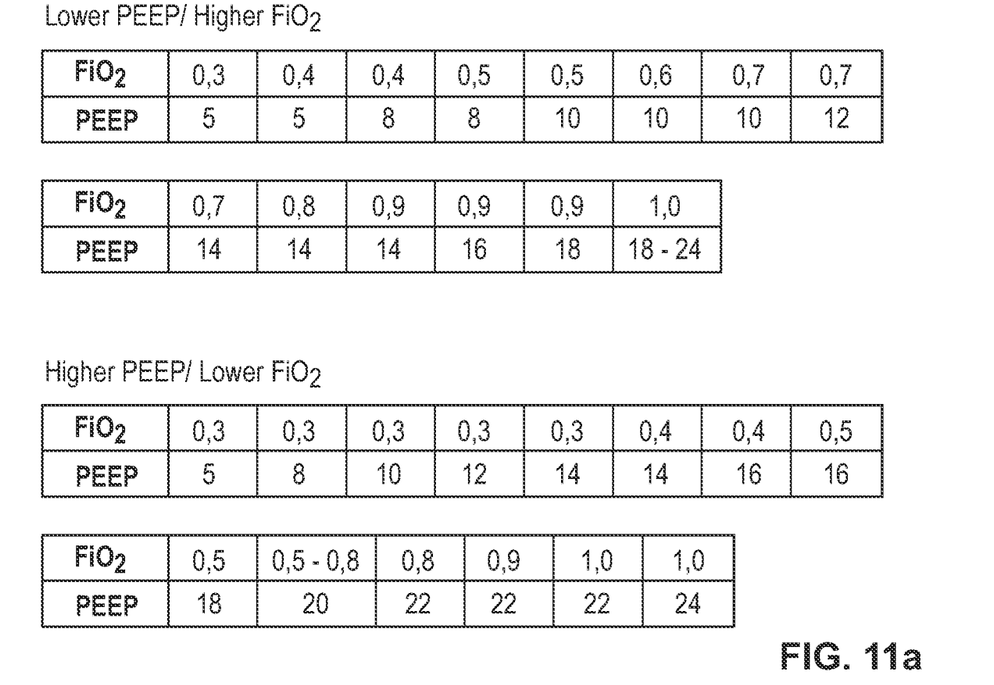
FIG. 11a is a view showing an example of a standard relation between ventilation gas parameters.
Figure 11B:
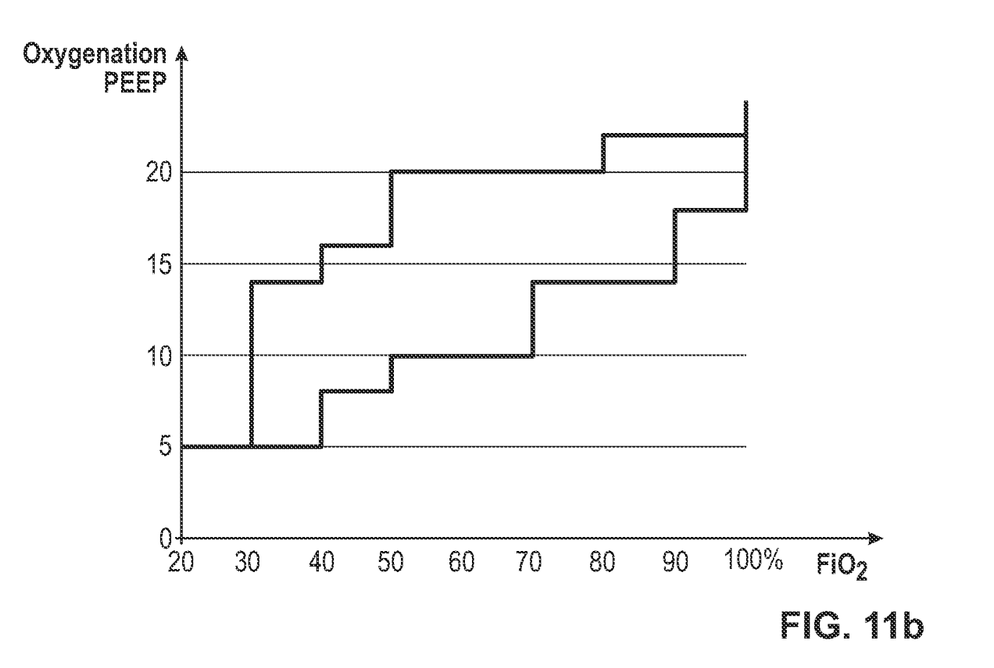
FIG. 11b is a graph showing the example of a standard relation between ventilation gas parameters.

According to the present invention, this is a relation for the ventilation parameters positive end-expiratory pressure (PEEP) and inspiratory O2 concentration (FiO2), as shown in an exemplary embodiment in FIG. 11. This is a recommendation for the connection between the PEEP value and the FiO2 value, as it is published by the ARDSnet expert committee for optimal oxygenation. The two value tables represent each characteristics for a lower limit as well as an upper limit of a connection between end-expiratory pressure, on the one hand, and the inspiratory oxygen concentration, on the other hand. The value table is shown in FIG. 11a, and FIG. 11b shows the characteristics arising therefrom. This is the definition of the relation 4 being used in the present example. As shown in FIG. 3, it is stored in a storage element 41. This is shown by way of symbols in FIG. 3 by means of two characteristics 73, 74 in a system of coordinates 70, the x axis 71 of which shows the FiO2 value for the oxygenation and the y axis 72 of which shows the PEEP value for the end-expiratory pressure. The optimal setting value combinations are determined by the characteristics 73 and 74 themselves in this system of coordinates 70. It is also possible that the characteristics define the limits of a permissible range, or even, vice versa, the limits of a forbidden range. Other relation conditions 4, not shown, may be contained in the other storage elements 42, 43.

If settings are made by the operator, whether it be by means of the virtual actuator 24 or by means of the physical actuator 23, then the deviation detector 31 of the relation monitor 3 checks whether or not the change made during the setting is permissible according to the relation 4. The display is carried out here by means of a pop-up window 7. As is clear from FIGS. 2 and 4, this is displayed by means of a pop-up window 7 (see the rectangular area defined by a dotted line in FIGS. 2 and 4) as a superimposed view on the display unit 21 in direct proximity to the actuator 24 used.

Figure 4:
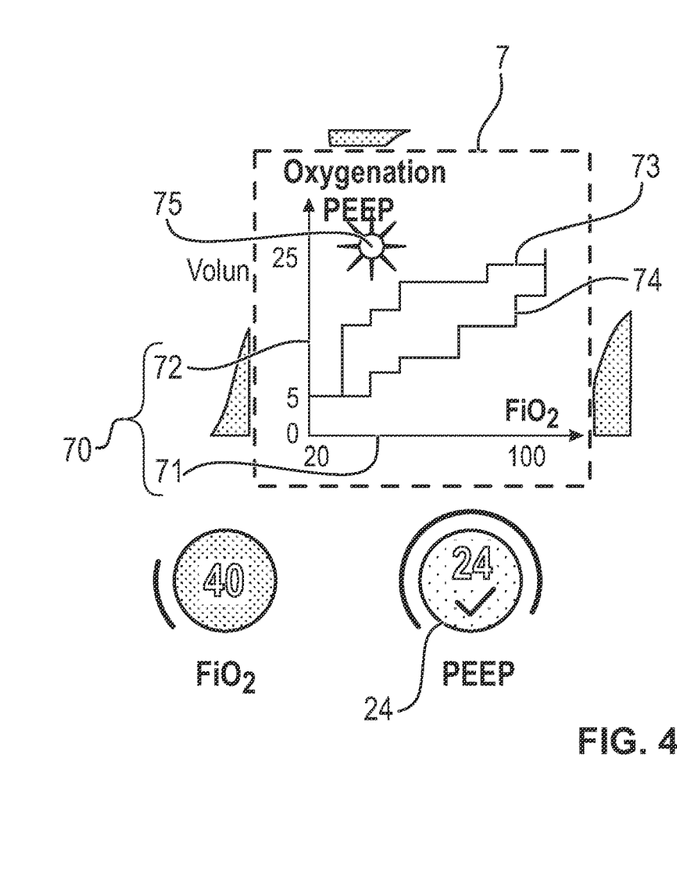
FIG. 4 is a view showing an exemplary embodiment for a pop-up window.

The case shown in FIG. 4 may be assumed to be an example that the PEEP value is set by the operator, namely the value is increased. As is shown by a marking 75, a large value is in this case currently set such that the upper characteristic 73 was left. The relation 4 is thus transgressed. The deviation detector 31 detects this and outputs a signal to a graphics module 6 via a warning unit 32, which signal makes the marking 75 flash and thus a warning signal is outputted to the operator. It should be noted that, as an alternative or in addition, additional warning signals can be outputted, for example, a warning sound, or that the marking 75 is highlighted in a different way, be it by a color change, an animation, a change in the background color, or the like. It should be noted that, as an alternative or in addition to the marking 75, the virtual actuator 24 may also be configured for the output of a warning signal in case of a transgression of the relation, so that it may possibly also take over or complement the function of the marking 75, as described below.

Figure 5A:
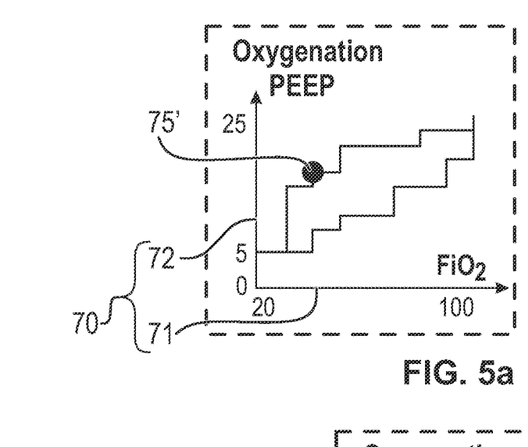
FIG. 5a is a view of an alternative display for the pop-up window.
Figure 5B:
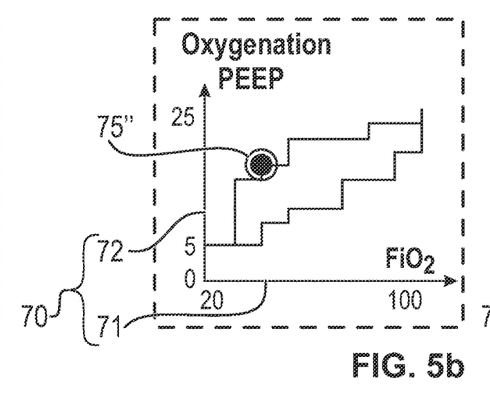
FIG. 5b is a view of another alternative display for the pop-up window.
Figure 5C:
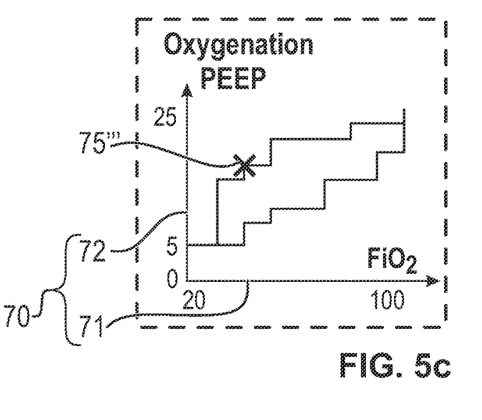
FIG. 5c is a view of another alternative display for the pop-up window.

The operator is thus clearly made aware of the transgression of the relation 4 and is able to correct the value even before it is sent to the control device 11. If the operator now retracts the value and finally again reaches the permissible range, so that the oxygenation can be rated as optimal, then the marking 75 used for the display is changed. FIGS. 5a, b and c show examples of this. A marking 75' having a different color, a marking 75" enclosed with an additional circle or even a marking 75'" having a different shape, configured here as a cross can thus be displayed when reaching an optimal setting value combination according to the relation 4. It is thus intuitively illustrated to the operator that a transgression of the relation 4 is now no longer present.

Furthermore, provisions may also optionally be made that a switch is routinely made back and forth between different types of marking in order to further draw the attention of the operator to same.

Figure 6:
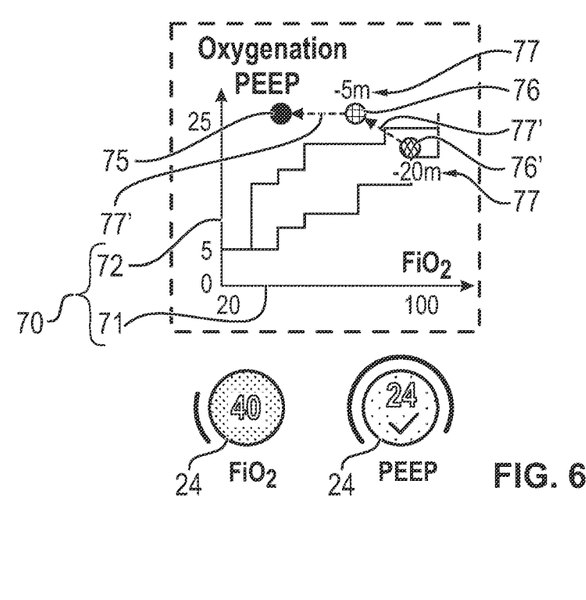
FIG. 6 is an view showing an exemplary embodiment for a pop-up window with history marker.

A display, in which the previously used setting value combination and the course over the last two setting value combinations used in the present case are displayed, is shown in FIG. 6. The current setting is shown by the marking 75. The previously used setting value combination is shown by the marking 76, and the even older setting value combination is shown by the marking 76'. Optionally, time markings 77 corresponding to these markings are provided, which indicate when these older setting value combinations were used. A view into the past setting values and the course over time thereof is thus made possible. The values from the past necessary for this are stored in a storage device 36 for previous setting values. As an alternative or in addition, the chronological sequence of the setting value combinations 76, 76' may also be displayed by arrows 77'. The course over time is thus present clearly for the operator.

Further, provisions may optionally be made to display a suggested value 78 for the next adjustment, which suggested value is calculated by a predictor module 5, starting from the present setting value combination shown by the marking 75, especially based on the current setting value combination, optionally from the relation 4 as well as optionally from the history of the setting value combinations that occurred most recently. To this end, the predictor module 5 interacts with an optional measuring unit 51 for patient measured values as well as with a target mark generator 50 that shows correspondingly a marking for the suggested value 78 in a pop-up window 7. Such a suggested value 78 may also be provided by a compensation module 37. This is configured to determine a new setting value, with which the relation condition 4 is still met in case of a transgression of the relation condition 4.

A verification unit 34 is optionally provided, which interacts with the deviation detector 31 and outputs a confirmation signal when a deviation is no longer present. The user thus immediately receives information if the transgression of the relation condition no longer exists.

Further, a default transmitter 35 with a storage device may optionally be provided, which is configured to set the preselected parameter to a security value and to send a signal about this preferably in a separate manner in case of transgression of the relation condition. Thus, the preselected parameter can be reached by means of the security value set by the default transmitter in the absence of a response by the operator. The security value may be, for example, the most recent previous value, with which no transgression of the relation condition was present, or a limit value for the preselected parameter that still meets the transgressed relation condition.

Figure 7:
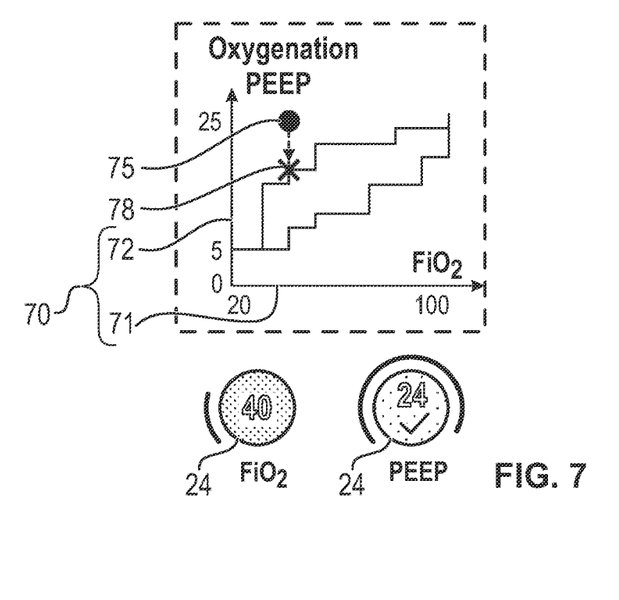
FIG. 7 is a view showing an exemplary embodiment for a pop-up window with target marking.
Figure 8:
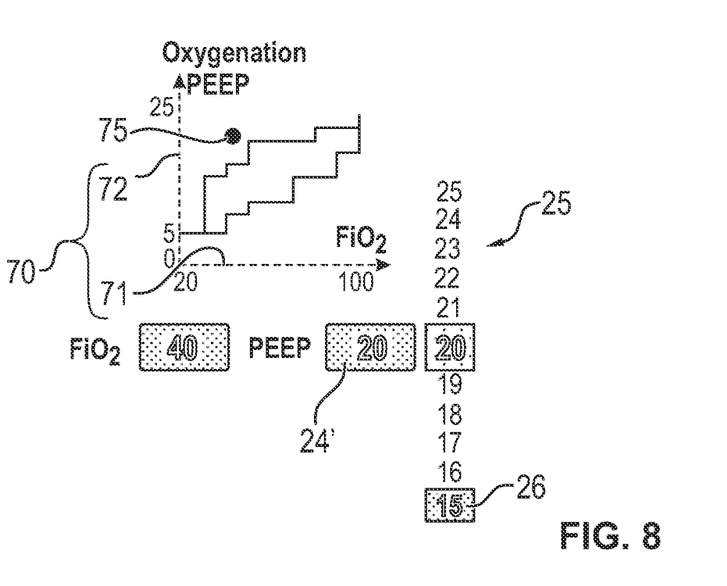
FIG. 8 is a view of a display for a virtual setting element with additional pop-up window.

Reference is now made to FIG. 8, which shows the setting by means of a virtual setting element 24'. This displays the currently selected setting value in a field adjacent to the pop-up window with the display of the system of coordinates 70. A scale 25 of possible setting values is shown next to it. The suggested value determined by the predictor module 5 is preferably highlighted there with a special marking 26, similar to the graphic view of the target mark 78 in FIG. 7. The operator can thus set the new value by simple scrolling on the scale 25, taking corresponding consideration of the suggested value 26. The position of this setting in relation to the system of coordinates 70 of the relation condition 4 is shown graphically by means of the marking 75 in pop-up windows.

Figure 9A:
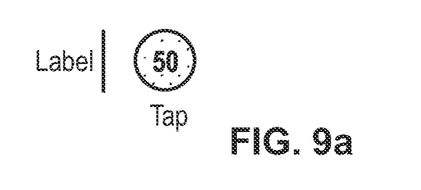
FIG. 9a is a schematic view showing a setting feature by means of the virtual setting element.
Figure 9B:
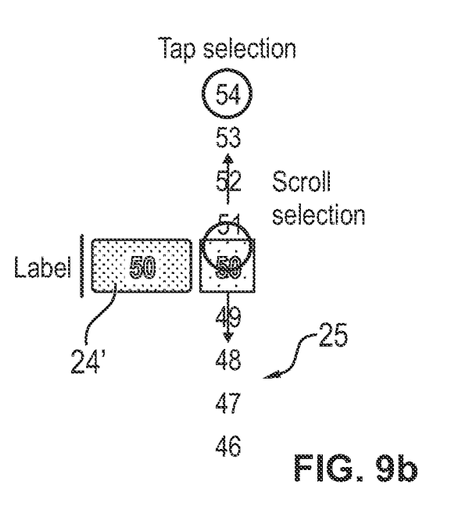
FIG. 9b is a schematic view showing the setting feature by means of the virtual setting element.
Figure 9C:
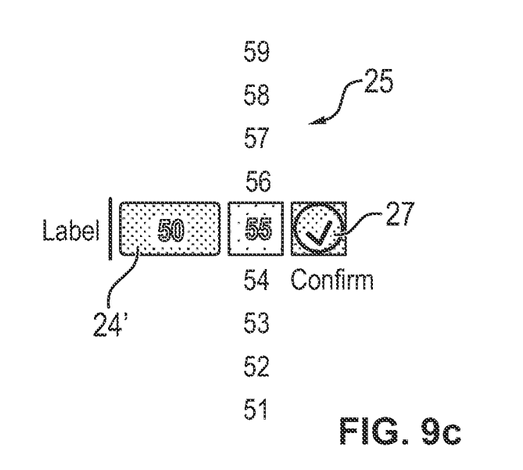
FIG. 9c is a schematic view showing the setting feature by means of the virtual setting element.

The setting of the values is preferably carried out with a virtual setting dial 24' as shown in FIGS. 9a-c. A "touch-tap/scroll-confirm" process is provided. In a first step shown in FIG. 9a, in this case, the parameter to be set, here symbolized by "label," is selected by means of touching, and in a second step shown in FIG. 9b, the desired new setting value is selected either by tapping on the desired new setting value or by scrolling of the scale 25, and finally in a third step shown in FIG. 9c, this value is confirmed, preferably after the relation condition 4 was positively checked.

Further, a counter-actuator 29 may be associated with the actuator 23, 24. This counter-actuator counteracts a further actuation of the operating element if the relation condition 4 is transgressed. In case of a physical actuator 23, this can take place by means of a force feedback actuator, which acts mechanically on the actuator 23. It preferably unidirectionally counteracts an actuation by the operator in such a way that the operator is thus haptically guided to the return from the transgressed relation condition. Correspondingly, provisions may be made in case of a virtual actuator 24 for the counter-actuator 29 to be reduced to the control signal generated by the virtual actuator 24, and in particular by means of a changed control characteristic.

Figure 10:
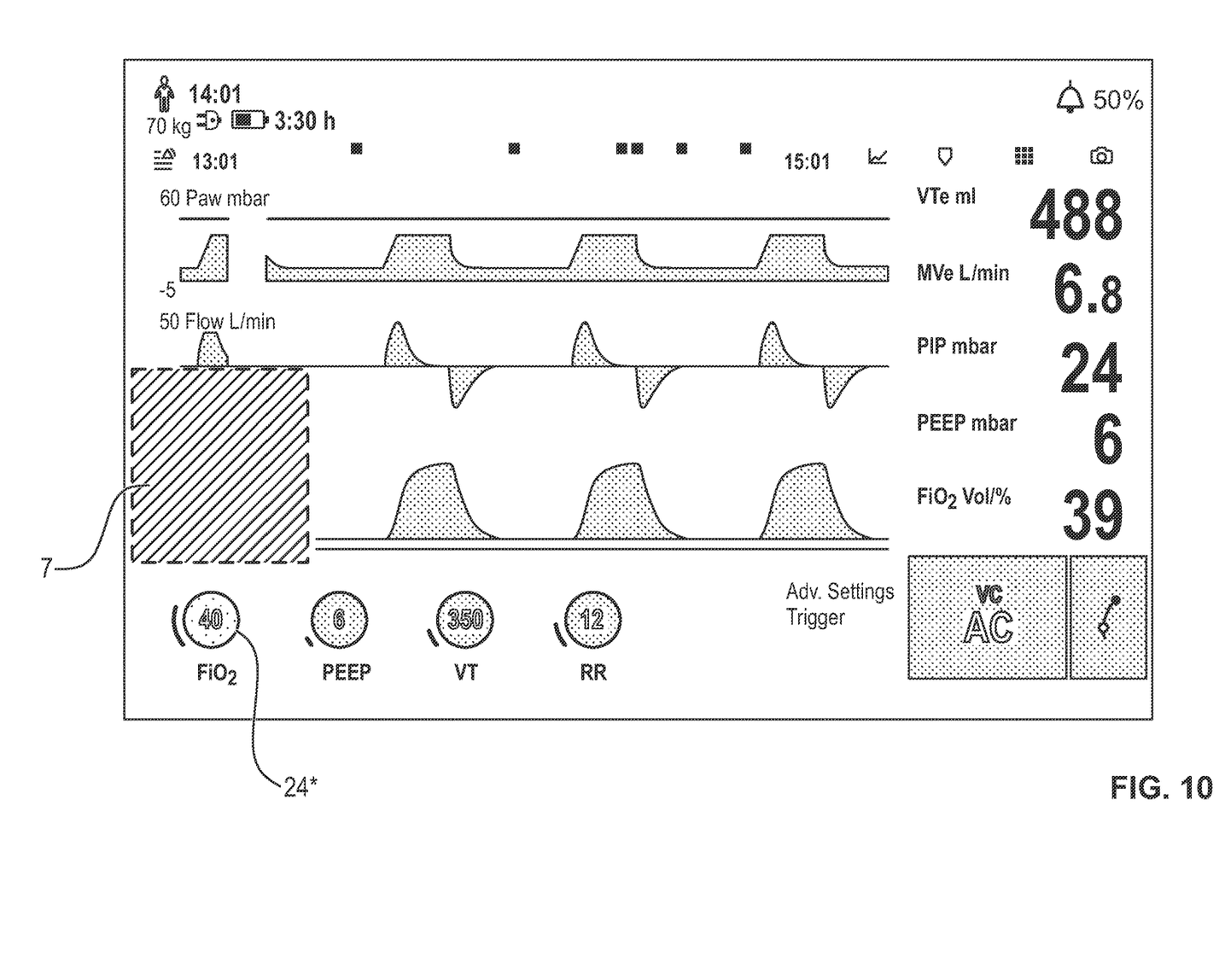
FIG. 10 is a view of a display on the display unit with alternative position of the pop-up window.

The display of the pop-up window 7 is not carried out statically at a point on the display unit 21, but the positioning is carried out in dynamic dependence on the set parameter. If, for example, the FiO2 value is being set rather than the PEEP value, as in the previous exemplary embodiments, the pop-up window 7 will be positioned differently as shown in FIG. 10, namely in direct proximity to the actuator 24 for the FiO2 value. Otherwise, the above description correspondingly applies to the display in the pop-up window. In case of the change of other parameters, the pop-up window 7 will again be correspondingly positioned differently.

While specific embodiments of the invention have been shown and described in detail to illustrate the application of the principles of the invention, it will be understood that the invention may be embodied otherwise without departing from such principles.

What is claimed is:

1. A ventilator operating unit for a ventilator comprising a gas dispensing device for ventilation gases and a gas dispensing-influencing and monitoring control unit, wherein the operating unit is configured to set at least two parameters of the control unit which are relevant to the ventilation and to send setting values for the parameters to the control unit, the operating unit comprising:
   a display unit for outputting the parameters;
   an input element for inputting a change to a preselected parameter, which is selected from the parameters which are relevant to the ventilation, wherein, after inputting the change of the preselected parameter, a new parameter setting value is sent to the control unit; and
   a relation monitor comprising:
      a relation storage module configured to store at least one relation condition between two or more of the parameters, wherein the relation condition stored in the relation storage module comprises a relation condition between an inspiratory oxygen fraction (FiO2) and a positive end-expiratory pressure (PEEP);
      a deviation detector configured to check the at least one relation condition of the preselected parameter to one or more of the other parameters, upon inputting the change to the preselected parameter setting and to detect whether the at least one relation condition is met or transgressed by the input change to the preselected parameter setting;
      a warning unit configured to interact with the deviation detector and to output corresponding warning information in case of a transgression; and
      a graphics module configured to display the at least one relation condition on the display unit as a superimposed view, wherein in case of the transgression of the relation condition, a current value of the preselected parameter is highlighted, shown with a marking in a system of coordinates, which shows the current value of the preselected parameter and the relation condition.

2. A ventilator operating unit in accordance with claim 1, wherein the superimposed view is movable on the display unit, such that the superimposed view is placed adjacent to a display view of the preselected parameter.

3. A ventilator operating unit in accordance with claim 1, wherein the graphics module is configured such that the current value of the preselected parameter is highlighted with a marking in case of the transgression of the relation condition, which highlighting is one or more of a color change, a contrast color, a symbol change, an additional symbol and a change of a background color.

4. A ventilator operating unit in accordance with claim 1, wherein the graphics module is configured to display the relation condition selectively visually as at least one of a value table, value corridors in a system of coordinates, and target corridors.

5. A ventilator operating unit in accordance with claim 1, wherein at least one of the relation storage module and the deviation detector is configured for multiparameter relations.

6. A ventilator operating unit in accordance with claim 1, further comprising a command element configured to interact with the deviation detector and to form and to display a signal for a corrected setting of the preselected parameter, with which the transgression of the relation condition is eliminated.

7. A ventilator operating unit in accordance with claim 1, further comprising a verification unit configured to interact with the deviation detector and to output a confirmation signal when a deviation is no longer present.

8. A ventilator operating unit in accordance with claim 1, further comprising a counter-actuator associated with the input element, wherein:
   the counter-actuator is configured to counteract a further actuation of the input element, at least unidirectionally, corresponding to a direction of a further transgression of the relation condition; and
   the counter-actuator generates a haptic feedback signal to the operator.

9. A ventilator operating unit in accordance with claim 1, further comprising a default transmitter with a storage device, wherein the default transmitter is configured to set the preselected parameter to a security value and to send a signal related to setting the preselected parameter to a security value in case of the transgression of the relation condition.

10. A ventilator operating unit in accordance with claim 1, further comprising a storage device for previous setting values of the parameters, wherein a history marker is provided, which selects at least one previous value for the selected parameter from the storage device and displays the at least one previous value for the selected parameter on the display device.

11. A ventilator operating unit in accordance with claim 1, further comprising a virtual setting element on the display unit, wherein a target mark, which represents at least one of an optimal value and a limit for meeting the relation condition, is additionally output on the display unit.

12. A ventilator operating unit in accordance with claim 1, further comprising a predictor module configured to determine a suggested value as a next value of the preselected parameter to be set from one or more of current setting values and previous setting values of the parameters which are relevant to the ventilation and/or from at least one of current patient measured values and previous patient measured values.

13. A ventilator operating unit in accordance with claim 12, further comprising a target mark generator, which interacts with the predictor module and which is configured to display a symbol in the superimposed view on the display view for a corresponding suggested value determined by the predictor module, wherein the predictor module interacts with the measuring unit for the patient measured values.

14. A ventilator operating unit in accordance with claim 1, further comprising a compensation module, wherein in the case of a transgressed relation condition, the compensation module determines a new setting value for one or more other parameters of the relation condition, with which new setting value the relation condition is met.

15. A ventilator operating unit in accordance with claim 14, further comprising an adjustment indicator generator, wherein the compensation module interacts with the adjustment indicator generator, whereby the adjustment indicator generator displays on the display device a symbol for a corresponding adjustment of the one or more other parameters of the relation condition.

* * * * *